(12) United States Patent
Okuda et al.

(10) Patent No.: US 8,759,108 B2
(45) Date of Patent: Jun. 24, 2014

(54) REAGENT KIT FOR DETECTING LUPUS ANTICOAGULANT AND METHOD OF DETERMINING PRESENCE OR ABSENCE OF LUPUS ANTICOAGULANT

(75) Inventors: Masahiro Okuda, Kobe (JP); Kazuyo Yoshida, Kobe (JP); Osamu Kumano, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 13/407,324

(22) Filed: Feb. 28, 2012

(65) Prior Publication Data

US 2012/0220038 A1 Aug. 30, 2012

(30) Foreign Application Priority Data

Feb. 28, 2011 (JP) ................................. 2011-042407

(51) Int. Cl.
  *G01N 33/86* (2006.01)
  *G01N 33/48* (2006.01)
(52) U.S. Cl.
  USPC ............ 436/69; 436/63; 436/73; 436/79; 422/430; 422/73; 600/369; 73/64.41
(58) Field of Classification Search
  USPC ........... 436/63, 69, 73, 74, 79, 100, 101, 102, 436/110, 119, 124; 422/430, 73; 435/13; 600/369; 73/64.41
  See application file for complete search history.

(56) References Cited

U.S. PATENT DOCUMENTS

| | | | | |
|---|---|---|---|---|
| 5,043,017 A | * | 8/1991 | Passaretti | 106/465 |
| 7,932,021 B2 | * | 4/2011 | Greenfield et al. | 435/2 |
| 2004/0091952 A1 | * | 5/2004 | Okuda | 435/13 |
| 2005/0175983 A1 | * | 8/2005 | Okuda | 435/4 |
| 2009/0061468 A1 | * | 3/2009 | Hoshiko et al. | 435/13 |
| 2009/0098585 A1 | * | 4/2009 | Okuda | 435/13 |
| 2012/0052585 A1 | * | 3/2012 | Okuda et al. | 436/69 |

FOREIGN PATENT DOCUMENTS

| | | |
|---|---|---|
| EP | 1562047 A1 | 8/2005 |
| JP | 2004-109034 A | 4/2004 |
| JP | 2006-133002 A | 5/2006 |
| WO | 2005/031303 A2 | 4/2005 |

OTHER PUBLICATIONS

Exner T et al: "Studies on Phospholipids in the Action of a Lupus Coagulation Inhibitor", Pathology, Modern Medicine, Sydney, AU, vol. 7, No. 4, Jan. 1, 1975, pp. 319-328, XP009160386.

Schjetlein R et al., "Choice of Standard Plasma for Diagnosis and Quantitation of Lupus Anticoagulants", Thrombisis Research, Tarrytown, NY, US, vol. 72, No. 4, Nov. 15, 1993, pp. 287-294, XP026405089.

Marlies Ledford-Kraemer, "Functional Laboratory Testing for the Lupus Anticoagulant", The Clotting Times, vol. 4, No. 4, Jan. 1, 2005, pp. 4-6, 9, XP55030599.

* cited by examiner

*Primary Examiner* — Maureen Wallenhorst
(74) *Attorney, Agent, or Firm* — Sughrue Mion, PLLC

(57) ABSTRACT

In order to provide a reagent kit for detecting LA which can clearly separate a lupus anticoagulant (LA)-positive specimen group from an LA-negative specimen group, it is configured that the reagent kit for detecting LA contains a first clotting time-measuring reagent and a second clotting time-measuring reagent and at least one of the first clotting time-measuring reagent and the second clotting time-measuring reagent contains alkali metal salt. The presence or absence of LA can be determined using the kit.

10 Claims, 3 Drawing Sheets

REAGENT KIT FOR DETECTING LUPUS ANTICOAGULANT AND METHOD OF DETERMINING PRESENCE OR ABSENCE OF LUPUS ANTICOAGULANT

FIELD OF THE INVENTION

The present invention relates to a reagent kit for detecting lupus anticoagulant which is one of the antibodies responsible for antiphospholipid syndrome and further relates to a method of determining the presence or absence of lupus anticoagulant in a specimen obtained from a subject.

BACKGROUND

Antiphospholipid syndrome (hereinafter, referred to as "APS") is a general term for a group of diseases which have antiphospholipid antibodies in the blood and present clinical symptoms such as arteriovenous thrombosis and habitual abortion (see Mika Yoshida et al., The Japanese Society for Laboratory Hematology, 2008, 9 (1):69-76). Antiphospholipid antibodies (hereinafter, referred to as "aPL") is a general term for autoantibodies which are bound to phospholipids or a complex of phospholipids and proteins (see Tatsuya Atsumi et al., The Japanese Society on Thrombosis and Hemostasis, 2008, 19 (3):329-332).

There are various antibodies aPL and the name of antibodies is given according to phospholipids recognized by the antibodies or phospholipid-binding proteins. Examples of the antibodies aPL include anti-cardiolipin antibodies (aCL), anti-β2 glycoprotein I antibodies (aβ2GPI), phosphatidylserine-dependent anti-prothrombin antibodies (aPS/PT), and lupus anticoagulant (hereinafter, also referred to as "LA"). aCL, aβ2GPI, and aPS/PT are detected by enzyme immunoassay (ELISA) and LA is detected by prolongation of phospholipid-dependent clotting time (see Masahiro Ieko et al., The Japanese Society on Thrombosis and Hemostasis, 2007, 18 (3):226-233).

LA is defined as "an immunoglobulin that inhibits phospholipid-dependent blood clotting reactions without inhibiting individual clotting factor activities. It is also considered that LA is an autoantibody that inhibits phospholipids themselves in the phospholipid-dependent blood clotting reactions.

Currently, the inspection standard of LA is as follows:
1) Prolongation of clotting time is observed in screening inspection for measuring phospholipid-dependent clotting times such as activated partial thromboplastin time (APTT), dilute Russel viper venom time (dRVVT), and kaolin clotting time (KCT);
2) The prolongation of clotting time is not improved even if mixing assay with plasma from healthy donors is performed;
3) It is confirmed that the clotting time is shortened by adding excessive phospholipids (test for assessing phospholipid dependence).

Finally, a subject is diagnosed to be LA-positive by excluding obvious clotting abnormalities such as inhibitors of clotting factors and influences of anticoagulants such as heparin (see Mika Yoshida et al., Journal of the Japanese Society for Laboratory Hematology, 2008, 9 (1):69-76).

One of the tests for assessing phospholipid dependence of LA is a method of assessing the presence of LA in a specimen including steps of: measuring the clotting time using a clotting time-measuring reagent which contains a low concentration of phospholipid and a clotting time-measuring reagent which contains a high concentration of phospholipid; and confirming the prolongation of clotting time depending on the phospholipid concentration based on a ratio of the clotting times obtained from the reagents.

The present inventors have completed a reagent kit capable of detecting LA at high sensitivity by adjusting the composition of phospholipid contained in a reagent (see U.S. Patent Publication No. 2004/0091952, U.S. Patent Publication No. 2005/0175983, and Japanese Patent Application Laid-Open (JP-A) No. 2006-133002).

Although LA can be detected by the above methods, prolongation of clotting time may be observed even if the reagent which contains a high concentration of phospholipid is used. That is, in the case of using the conventional methods, even a ratio of clotting time in an LA-positive specimen may be equal to that of a negative specimen. Thus, it is difficult to clearly separate an LA-positive specimen group from an LA-negative specimen group.

SUMMARY OF THE INVENTION

The scope of the present invention is defined solely by the appended claims, and is not affected to any degree by the statements within this summary.

The present inventors have found that the prolongation of the clotting time by LA can be suppressed by using a clotting time-measuring reagent containing alkali metal salt so that the LA-positive specimen group can be clearly separated from the LA-negative specimen group and the present invention has been completed.

A first aspect of the present invention is a reagent kit for detecting lupus anticoagulant comprising:
a first clotting time-measuring reagent; and
a second clotting time-measuring reagent;
wherein at least one of the first clotting time-measuring reagent and the second clotting time-measuring reagent contains alkali metal salt.

A second aspect of the present invention is a method of determining the presence or absence of lupus anticoagulant comprising steps of:
mixing a specimen taken from a subject with the first clotting time-measuring reagent containing alkali metal salt to measure the first clotting time;
mixing the specimen with the second clotting time-measuring reagent which contains alkali metal salt at a concentration lower than that of the first clotting time-measuring reagent or does not contain alkali metal salt to measure the second clotting time; and
determining whether LA is contained in the specimen based on the measured first and second clotting times.

According to the reagent kit for detecting LA of the present invention, prolongation of the clotting time by LA is suppressed so that the LA-positive specimen group can be clearly separated from the LA-negative specimen group. According to the method of determining the presence or absence of LA of the present invention, it can be accurately determined whether LA is contained in the specimen obtained from the subject.

DETAILED DESCRIPTION OF THE PREFERRED EMBODIMENTS

Figure 1:
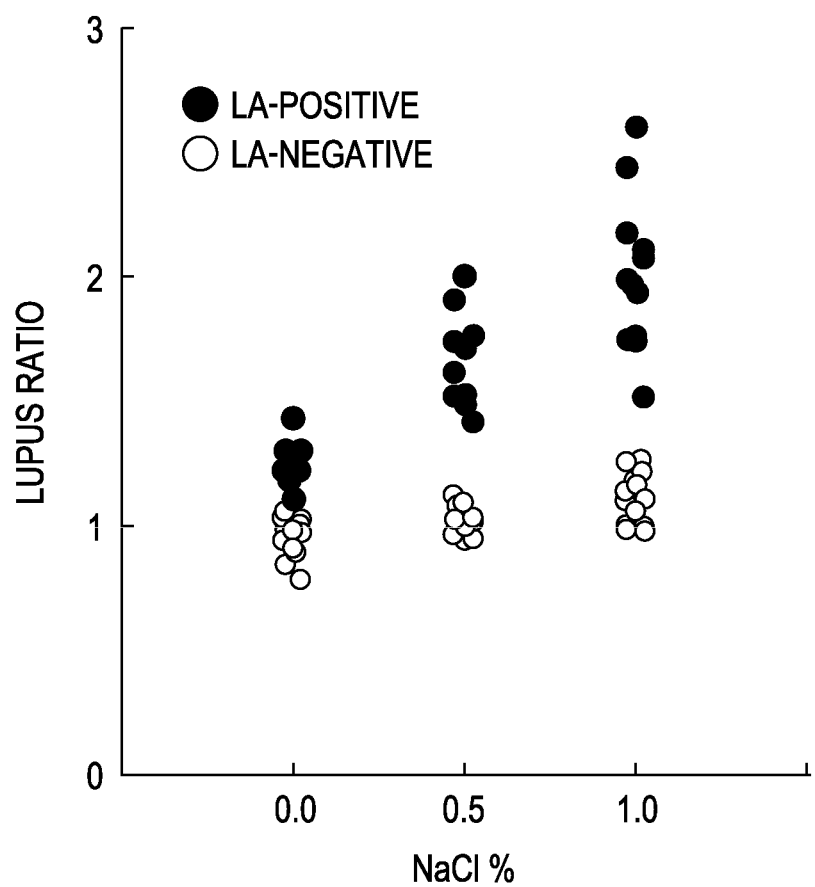
FIG. 1 is a scatter diagram showing distribution of the Lupus Ratio of LA-negative and LA-positive specimens which has been calculated from the clotting time measured using the reagent kit for detecting LA of the present invention which includes a first clotting time-measuring reagent which contains sodium chloride as alkali metal salt and a second clotting time-measuring reagent which does not contain alkali metal salt.

The preferred embodiments of the present invention will be described hereinafter with reference to the drawings.

The reagent kit for detecting LA of the present invention includes a first clotting time-measuring reagent and a second clotting time-measuring reagent where at least one of the first clotting time-measuring reagent and the second clotting time-measuring reagent contains alkali metal salt. Preferably, the reagent kit for detecting LA contains the first clotting time-measuring reagent containing alkali metal salt and the second clotting time-measuring reagent which contains alkali metal salt at a concentration lower than that of the first clotting time-measuring reagent or does not contain alkali metal salt. Hereinafter, the case where the first clotting time-measuring reagent containing alkali metal salt and the second clotting time-measuring reagent which contains alkali metal salt at a concentration lower than that of the first clotting time-measuring reagent or does not contain alkali metal salt are included as the reagent kit of the present invention will be described.

The alkali metal salt contained in the first and second clotting time-measuring reagents of the reagent kit of the present invention is not particularly limited as long as it generates alkali metal ions in an appropriate solvent, preferably buffers included in the reagents and anions generated from the alkali metal salt do not inhibit a blood-clotting reaction. Usable examples of alkali metal salt include inorganic acid alkali metal salts which are alkali metal salts such as hydrochloric acid, sulfuric acid, and nitric acid. Particularly, it is preferable to use inorganic acids such as sodium salts and potassium salts. Specific examples thereof include sodium chloride, sodium sulfate, sodium nitrate, potassium chloride, and potassium nitrate. Particularly, sodium chloride, sodium sulfate, and potassium chloride are preferred. The alkali metal salt may be an anhydride or a hydrate.

The concentration of alkali metal salt in the first clotting time-measuring reagent is from 0.001 to 40%, preferably from 0.01 to 10%, more preferably from 0.1 to 5%. The second clotting time-measuring reagent does not need to contain the alkali metal salt. When the second clotting time-measuring reagent contains the alkali metal salt, the concentration of alkali metal salt therein is preferably lower than that of the first clotting time-measuring reagent. For example, when the concentration of alkali metal salt in the first clotting time-measuring reagent is 1%, the concentration of alkali metal salt in the second clotting time-measuring reagent can be set to 0.1%.

In the reagent kit of the present invention, a ratio of concentration of alkali metal salt in the second clotting time-measuring reagent to the first clotting time-measuring reagent [alkali metal salt concentration of the second clotting time-measuring reagent]/[alkali metal salt concentration of the first clotting time-measuring reagent] is from 0 to 1, preferably from 0 to 0.2.

In the reagent kit of the present invention, it is preferable that the first clotting time-measuring reagent contains phospholipid and the second clotting time-measuring reagent contains phospholipid at a concentration lower than that of the first clotting time-measuring reagent in order to facilitate blood clotting.

Examples of the phospholipid include phosphatidylethanolamine (hereinafter also referred to as PE), phosphatidylcholine (hereinafter also referred to as PC), and phosphatidylserine (hereinafter also referred to as PS). The first and second clotting time-measuring reagents contain at least one selected from PE, PC, and PS, preferably two kinds thereof, more preferably all kinds of the phospholipids.

The phospholipid contained in the first and second clotting time-measuring reagents may be a naturally occurring phospholipid or a synthetic phospholipid. Among them, the synthetic phospholipid or the naturally occurring phospholipid purified with a purity of 99% or more is preferred from the viewpoint of improving the detectability of LA. The fatty acid side chains of PE, PC, and PS are not particularly limited and examples thereof include palmitic acid, oleic acid, and stearic acid. Among them, oleic acid is preferred.

The content of phospholipid in the first and second clotting time-measuring reagent when mixing equivalent amounts of a specimen and the first or second clotting time-measuring reagent are mixed (for example, mixing 50 µl of the specimen and 50 µl of the first or second clotting time-measuring reagent) and measuring the clotting time is as follows. The concentration of phospholipid in the first clotting time-measuring reagent is from 100 to 2000 µg/ml, preferably from 100 to 600 µg/ml. The concentration of phospholipid in the second clotting time-measuring reagent is from 20 to 100 µg/ml, preferably from 30 to 70 µg/ml.

In the above-described case, when the first and second clotting time-measuring reagents contain PE, PC, and PS as phospholipids, the concentration of PE in the first clotting time-measuring reagent is from 30 to 700 µg/ml, preferably from 40 to 300 µg/ml. The concentration of PC is from 50 to 1000 µg/ml, preferably from 60 to 500 µg/ml, and the concentration of PS is from 5 to 300 µg/ml, preferably from 10 to 150 µg/ml. The concentration of PE in the second clotting time-measuring reagent is from 1 to 100 µg/ml, preferably from 10 to 80 µg/ml. The concentration of PC is from 5 to 200 µg/ml, preferably from 20 to 150 µg/ml. The concentration of PS is from 1 to 100 µg/ml, preferably from 3 to 50 µg/ml.

When a mixed ratio of a specimen and the first or second clotting time-measuring reagent is not 1:1, the final concentration of phospholipid in a mixture of the specimen and the first or second clotting time-measuring reagent may be adjusted so as to be the same as a mixture when using reagents having the concentrations of phospholipids.

In the reagent kit of the present invention, the first and second clotting time-measuring reagents may further contain other components necessary to cause blood clotting in vitro. Examples of the other components include an activator, snake venom, a tissue factor, and calcium salt.

As the activator, at least one selected from the group consisting of ellagic acid, kaolin, celite, and silica is preferably used. The ellagic acid may be in a state where metal ions and chelate are formed.

As the snake venom, at least one selected from the group consisting of Russel's venom, textarin venom and ecarin venom is preferably used.

As the tissue factor, one derived from rabbit brain, derived from human placenta, or a recombinant is preferably used.

The above other components are suitably selected depending on the method of measuring the clotting time of the specimen. For instance, when the clotting time is measured based on the principle of an activated partial thromboplastin time, the first and second clotting time-measuring reagents may contain an activator and calcium salt. When the clotting time is measured based on the principle of a Russel's venom time, the first and second clotting time-measuring reagents may contain snake venom and calcium salt. When the clotting time is measured based on the principle of a prothrombin time, the first and second clotting time-measuring reagents may contain a tissue factor and calcium salt.

When the first and second clotting time-measuring reagents contain kaolin and calcium salt and the clotting time is measured based on the principle of a kaolin clotting time, endogenous phospholipids contained in the specimen are used for coagulation reaction. Thus, the first and second clotting time-measuring reagents do not need to contain the above-described phospholipids.

In the reagent kit of the present invention, the first clotting time-measuring reagent and second clotting time-measuring reagents may contain a buffer that has a buffering action in a pH range of 5 to 10, preferably a pH range of 6 to 9. Examples of the buffer include 4-(2-hydroxyethyl)piperazine-1-yl-ethane sulfonic acid (HEPES), tris(hydroxymethyl)aminomethane (Tris), and a phosphate buffer (PBS).

The concentration of the buffer in the reagents may be in a range allowable and generally used in the field of clinical chemistry, and is determined empirically based on simplified and repeated experiments.

The first clotting time-measuring reagent of the reagent kit of the present invention may be a mixture in a solution or suspension form which contains alkali metal salt and the phospholipid and/or other components in the buffer. Further, the second clotting time-measuring reagent may be a mixture in a solution or suspension form which contains the phospholipid and/or other components in the buffer and contains or does not contain alkali metal salt.

The reagent kit of the present invention may further contain a third clotting time-measuring reagent containing calcium salt. The calcium salt is not particularly limited as long as it generates calcium ions ($Ca^{2+}$) in an appropriate solvent, preferably buffers included in the reagents. For example, calcium chloride is cited. The concentration of calcium salt in the third clotting time-measuring reagent is not particularly limited as long as it is a concentration sufficient for initiation of coagulation in the mixture of the specimen and the first or second clotting time-measuring reagents, and it is preferably from 10 to 40 mM.

The reagent kit of the present invention may be a combined form of the first or second clotting time-measuring reagent and the third clotting time-measuring reagent. That is, in the reagent kit of the present invention, the first clotting time-measuring reagent may be comprised of the first partial reagent containing alkali metal salt and the second partial reagent containing calcium salt. The second clotting time-measuring reagent may comprised of the third clotting time-measuring reagent which contains alkali metal salt at a concentration lower than that of the first clotting time-measuring reagent or does not contain alkali metal salt and a fourth partial reagent containing calcium salt.

Hereinafter, the method of determining the presence or absence of LA in a specimen (also referred to as a method of the present invention) will be described. In the method of the present invention, the reagent kit for detecting LA of the present invention is suitably used.

In the method of the present invention, a specimen taken from a subject is first mixed with the first clotting time-measuring reagent containing alkali metal salt and the first clotting time is measured.

The specimen used in the measurement is blood obtained from the subject, preferably plasma obtained from the blood, more preferably plasma after removal of platelets. Furthermore preferably, a mixture of plasma from the subject and normal plasma or normal plasma after removal of platelets is used as the specimen. Using a mixture containing normal plasma as a specimen is advantageous in preventing prolongation of clotting time resulting from a clotting factor deficiency in the subject as well as improving detection sensitivity in a test of detecting phospholipid-dependent blood clotting disorder. The mixing ratio of the plasma from the subject to normal plasma generally ranges from 4:1 to 1:4, and preferably is 1:1.

In the method of the present invention, the specimen is divided into two parts. One is used to measure the first clotting time and the other is used to measure the second clotting time.

One of the two divided specimens is mixed with the first clotting time-measuring reagent. When the reagent is comprised of the first partial reagent and the second partial reagent, the specimen may be mixed with a mixture of the first partial reagent and the second partial reagent or a mixture of the specimen and the first partial reagent (or the second partial reagent) may be mixed with the second partial reagent (or the first partial reagent).

The mixing ratio (volume ratio) of the first clotting time-measuring reagent and the specimen may be from about 4:1 to 1:4, preferably 1:1.

When the first partial reagent and the second partial reagent are separately added to the specimen, a mixture of the specimen and the partial reagent may be incubated after adding the first partial reagent (or the second partial reagent) and before adding the second partial reagent (or the first partial reagent), if necessary. The time of incubation may be from about 1 to 10 minutes and the temperature may be from about room temperature to 45° C.

The specimen and the first clotting time-measuring reagent are mixed in such a manner and then the first clotting time is measured. The method of measuring the clotting time may be a known method in the art, and can be measured, for example, by using a known automated analyzer.

Then, the specimen is mixed with the second clotting time-measuring reagent which contains alkali metal salt at a concentration lower than that of the first clotting time-measuring reagent or does not contain alkali metal salt, and the second clotting time is measured.

The second clotting time is measured by mixing the other of the two divided specimens with the second clotting time-measuring reagent. More particularly, the measurement process is performed in the same manner as described in the measurement of the first clotting time except that the second clotting time-measuring reagent is used in place of the first clotting time-measuring reagent.

The first and second clotting times may be measured successively or simultaneously.

On the basis of the first and second clotting times measured as described above, it is determined whether LA is contained in the specimen. Specifically, it is preferable that the process of determining the presence or absence of LA in the specimen is performed using values obtained based on the first and second clotting times.

Examples of the values obtained based on the first and second clotting times include the difference or ratio between the first and second clotting times. Examples of the difference include a value calculated from the equation: "(the second clotting time)–(the first clotting time)" and a value calculated from the equation: "(the first clotting time)–(the second clotting time)". Examples of the ratio include a value calculated from the equation: "(the second clotting time)/(the first clotting time)" and a value calculated from the equation: "(the first clotting time)/(the second clotting time)".

In the reagent kit of the present invention, the prolongation of the first clotting time by LA is suppressed by alkali metal salt in the first clotting time-measuring reagent. Therefore, it is predicted that the first clotting time is equal to or shorter than the second clotting time.

Consequently, in the case where, for example, the value calculated from the equation: "(the second clotting time)–(the first clotting time)" is used as the difference of the first and second clotting times in the determination process, it can be determined that LA is present in the specimen obtained from the subject when the value is large. On the contrary, when a value calculated from the equation: "(the second clotting time)–(the first clotting time)" is small (0 or a negative value is included), it can be determined that LA is not present in the specimen.

In the case where the presence or absence of LA in the specimen is determined using, for example, the value calculated from the equation: "(the second clotting time)/(first clotting time)" as the ratio of the first clotting time and the second clotting time, it can be evaluated that LA is present in the specimen when the ratio is large. On the contrary, when the value calculated from the equation: "(the second clotting time)/(the first clotting time)" is small, it can be determined that LA is not present in the specimen.

The process of determining the presence or absence of LA in the specimen can be experientially performed by accumulating data of the first and second clotting times about specimens obtained from healthy subjects and LA subjects, respectively. From the viewpoint of more accurate determination, it is preferable that the process of determining the presence or absence of LA in the specimen is performed based on the results obtained by comparing a value obtained based on the first and second clotting times obtained from the specimen of the subject to a threshold value to be described later.

It is preferable that the threshold value is determined based on a ratio of the clotting time of the specimen obtained from the subject to the clotting time of normal plasma such as, for example, Rosner Index (E. Rosner et al., Thromb. Haemast. 1987, 57:144-147) or Lupus Ratio (also referred to as an LR value) (R. Schjetlein et al., Thromb. Res. 1993, 69:239-250).

The term "Lupus Ratio (LR value)" herein means a value calculated by Equation (I) below.

$$\text{Lupus Ratio} = (b/a)/(d/c) = bc/ad \quad \text{Equation (I)}$$

(in Equation (I), a, b, c, and d respectively represent measured values as follows: a: clotting time obtained from the specimen of the subject and the first clotting time-measuring reagent; b: clotting time obtained from the specimen of the subject and the second clotting time-measuring reagent; c: clotting time obtained from a specimen of a healthy subject (normal plasma) and the first clotting time-measuring reagent; and d: clotting time obtained from the specimen of a healthy subject (normal plasma) and the second clotting time-measuring reagent).

In the case of normal plasma, the LR value is around 1. Likewise, the LR value of each of the specimens from patients with blood clotting factor deficiency, patients administered with warfarin, or patients administered with heparin is around 1 because there is little recognition of a difference between the first and second clotting times despite the fact that the clotting time is longer as compared with the case of normal plasma. On the other hand, in the case of specimens obtained from LA-positive patients, the second clotting time is longer than the first clotting time due to the presence of LA in the specimen, and thus the LR value of LA-positive patients is larger than 1. Accordingly, specimens containing LA, i.e., specimens derived from LA-positive patients can be automatically detected by comparing to the LR value of normal plasma.

The alkali metal salt which may be included in the first and second clotting time-measuring reagents to be used in the method of the present invention is not particularly limited as long as it generates alkali metal ions in an appropriate solvent, preferably buffers included in the reagents and do not inhibit a phospholipid-dependent blood-clotting reaction. Usable examples of alkali metal salt include inorganic acid alkali metal salts which are alkali metal salts such as hydrochloric acid, sulfuric acid, and nitric acid. Particularly, it is preferable to use inorganic acids such as sodium salts and potassium salts. Specific examples thereof include sodium chloride, sodium sulfate, sodium nitrate, potassium chloride, and potassium nitrate. Particularly, sodium chloride, sodium sulfate, and potassium chloride are preferred. The alkali metal salt may be an anhydride or a hydrate.

It is preferable that the first clotting time-measuring reagent to be used for the method of the present invention contains phospholipid and the second clotting time-measuring reagent contains phospholipid at a concentration lower than that of the first clotting time-measuring reagent. The phospholipid is at least one selected from the group consisting of phosphatidylethanolamine, phosphatidylcholine, and phosphatidylserine.

The first and second clotting time-measuring reagents to be used for the method of the present invention may contain other components such as an activator, snake venom, a tissue factor, and calcium salt. Examples of the activator include ellagic acid, kaolin, celite, and silica.

Hereinafter, Examples will be explained, however, the present invention is not limited thereto.

EXAMPLES

It was examined whether the LA-positive and LA-negative specimens can be clearly separated with a reagent for detecting LA containing alkali metal salt.

Reagents for detecting LA (two reagent systems) based on the principle of an activated partial thromboplastin time were prepared. As for the reagents for detecting LA, a reagent containing alkali metal salt and phospholipid is referred to as "LA-H" and a reagent containing phospholipid at a concentration lower than that of LA-H is referred to as "LA-L". The reagent LA-H is composed of the first partial reagent and the second partial reagent and the reagent LA-L is composed of the third partial reagent and the fourth partial reagent.

The first partial reagent contained 50 mM of HEPES (Kishida Chemical Co., Ltd.), 0.1 mM of ellagic acid (Kishida Chemical Co., Ltd.), 25 mM of Tris (Kishida Chemical Co., Ltd.), 60 µg/ml PE (Nacalai Tesque, Inc.), 120

μg/ml PC (Nacalai Tesque, Inc.), and 20 μg/ml PS (Nacalai Tesque, Inc.), and sodium chloride as alkali metal salt (at a final concentration of 0.5 wt % and 1.0 wt %, Nacalai Tesque, Inc.). First partial reagents which respectively contain sodium sulfate (at a final concentration of 0.5 wt % and 1.0 wt %, Nacalai Tesque, Inc.) and potassium chloride (at a final concentration of 0.5 wt % and 1.0 wt %, Kishida Chemical Co., Ltd.) as alkali metal salt were prepared. Each of the first partial reagents includes ellagic acid containing a metal salt and chelate formed. As a control of the first partial reagent, a reagent without containing alkali metal chloride salt was also prepared. The pH of these reagents was adjusted to 7.35.

The third partial reagent contains 50 mM of HEPES (Kishida Chemical Co., Ltd.), 0.1 mM of ellagic acid (Kishida Chemical Co., Ltd.), 25 mM of Tris (Kishida Chemical Co., Ltd.), 15 μg/ml of PE (Nacalai Tesque, Inc.), 30 μg/ml of PC (Nacalai Tesque, Inc.), and 5 μg/ml of PS (Nacalai Tesque, Inc.). The third partial reagent includes ellagic acid containing a metal salt and chelate formed. The pH of the third partial reagent was adjusted to 7.35.

The second and fourth partial reagents were a solution prepared by dissolving calcium chloride (molecular weight: 111.0, Kishida Chemical Co., Ltd.) in purified water at a final concentration of 25 mM.

2. Measurement Samples

The used LA-negative specimens were a normal sample, Coagtrol N (SYSMEX CORPORATION), plasma from 11 healthy donors (SUNFCO LTD.), heparinized plasma from 1 patient (plasma prepared by adding unfractionated heparin (Mochida Pharmaceutical Co., Ltd.) to Coagtrol N at a final concentration of 0.5 U/ml), plasma from 3 patients having a clotting factor deficiency (George King Bio-Medical, Inc), and plasma from 2 patients administered with warfarin (George King Bio-Medical, Inc).

The used LA-positive specimens were plasma from 11 LA-positive patients (SUNFCO LTD.).

3. Measurement of Clotting Times

Two sets of 50 μl of the specimens were prepared. Specimens of one of the sets were mixed with 50 μl of the first partial reagent. Specimens of the other set were mixed with 50 μl of the third partial reagent. The resultant mixtures were heated at 37° C. for 3 minutes. Thereafter, those mixtures were mixed with 50 μl of the second partial reagent (or the fourth partial reagent) and the clotting time was measured. The clotting time was measured with an automated blood coagulation analyzer "Coagrex-800" (Shimadzu Corp.).

4. Calculation of Lupus Ratio

The Lupus Ratio of was calculated from the clotting times obtained by measuring the clotting time of each specimen according to the following equation.

$$(\text{Lupus Ratio}) = (b/a)/(d/c) = bc/ad \qquad \text{Equation}$$

(in Equation, a, b, c, and d respectively represent measured values as follows: a: clotting time obtained from the LA specimen and the reagents LA-H; b: clotting time obtained from the LA specimen and the reagent LA-L, c: clotting time obtained from the normal sample and the reagents LA-H; and d: clotting time obtained from the normal sample and the reagent LA-L).

Figure 2:
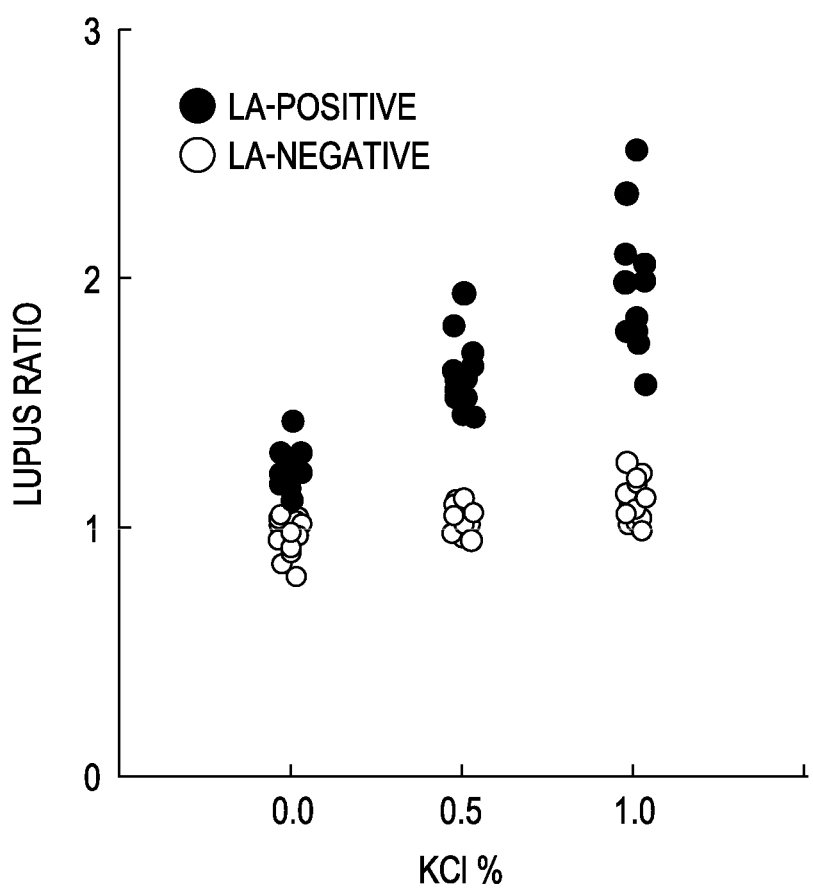
FIG. 2 is a scatter diagram showing distribution of the Lupus Ratio of LA-negative and LA-positive specimens which has been calculated from the clotting time measured using the reagent kit for detecting LA of the present invention which includes the first clotting time-measuring reagent which contains potassium chloride as alkali metal salt and the second clotting time-measuring reagent which does not contain alkali metal salt.
Figure 3:
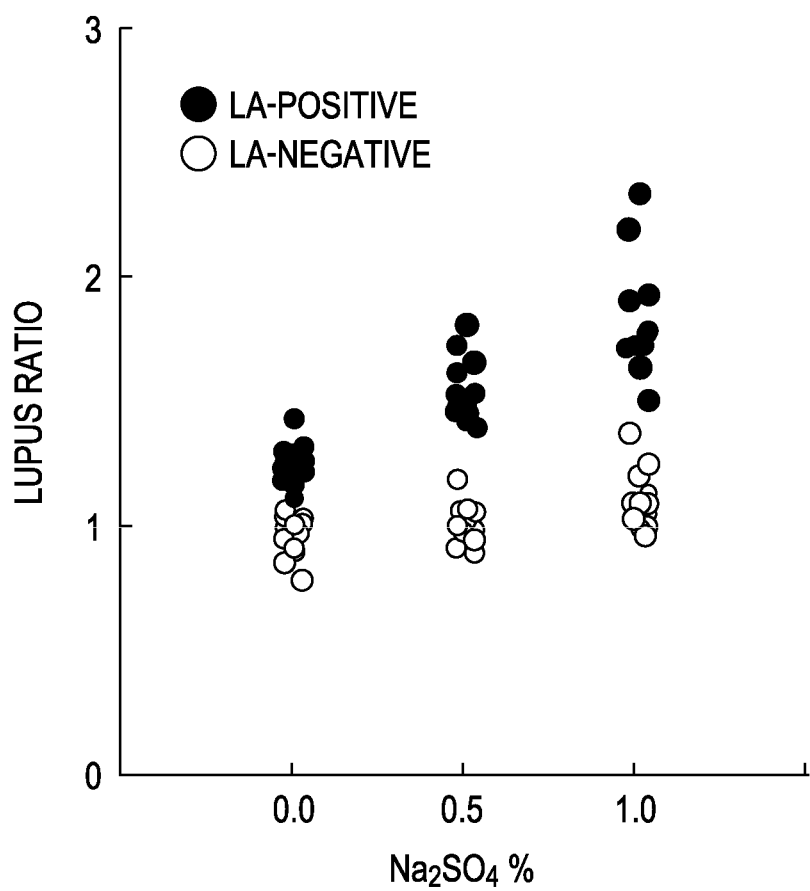
FIG. 3 is a scatter diagram showing distribution of the Lupus Ratio of LA-negative and LA-positive specimens which has been calculated from the clotting time measured using the reagent kit for detecting LA of the present invention which includes the first clotting time-measuring reagent which contains sodium sulfate as alkali metal salt and the second clotting time-measuring reagent which does not contain alkali metal salt.

The distribution of the Lupus Ratio concerning each of the reagents for detecting LA which has been calculated from the LA-negative specimen and the LA-positive specimen is shown in FIGS. 1 to 3. FIGS. 1 to 3 show that the Lupus Ratio of the LA-positive specimen is increased in the measurement system using the reagent containing alkali metal salt. Therefore, it has been confirmed that the reagent kit for detecting LA of the present invention can more clearly separate the LA-positive specimen from the LA-negative specimen as compared to conventional reagent kits without containing alkali metal salt.

What is claimed is:

1. A method of determining the presence or absence of lupus anticoagulant comprising steps of:
   mixing a first specimen taken from a subject with a first clotting time-measuring reagent containing phospholipid and alkali metal salt to measure a first clotting time;
   mixing a second specimen taken from the subject with a second clotting time-measuring reagent which contains phospholipid, and contains alkali metal salt at a concentration lower than that of the first clotting time-measuring reagent or does not contain alkali metal salt to measure a second clotting time; and
   determining whether lupus anticoagulant is contained in the first and second specimens based on the difference or ratio between the measured first and second clotting times, wherein if lupus anticoagulant is contained in the first and second specimens, the first clotting time is shorter than the second clotting time;
   wherein the first and second clotting time-measuring reagents contain an activator, snake venom, or tissue factor.

2. The method of determining the presence or absence of lupus anticoagulant according to claim 1, wherein
   it is determined whether lupus anticoagulant is contained in the first and second specimens by comparing a value obtained based on the difference or ratio between the first and second clotting times to a predetermined threshold value in the determination step.

3. The method of determining the presence or absence of lupus anticoagulant according to claim 1, wherein
   the first clotting time-measuring reagent contains phospholipid and the second clotting time-measuring reagent contains phospholipid at a concentration lower than that of the first clotting time-measuring reagent.

4. The method of determining the presence or absence of lupus anticoagulant according to claim 1, wherein
   the alkali metal salt is inorganic acid alkali metal salt.

5. The method of determining the presence or absence of lupus anticoagulant according to claim 1, wherein
   the alkali metal salt is sodium salt or potassium salt.

6. The method of determining the presence or absence of lupus anticoagulant according to claim 1, wherein
   the activator is selected from the group consisting of ellagic acid, kaolin, celite, and silica.

7. The method of determining the presence or absence of lupus anticoagulant according to claim 1, wherein
   the phospholipid is at least one selected from the group consisting of phosphatidylethanolamine, phosphatidylcholine, and phosphatidylserine.

8. A reagent kit for detecting lupus anticoagulant comprising:
   a first clotting time-measuring reagent containing phospholipid and alkali metal salt; and
   a second clotting time-measuring reagent containing phospholipid at a concentration lower than that of the first clotting time-measuring reagent, and containing alkali metal salt,
   wherein the alkali metal salt in the second clotting time-measuring reagent is present at a concentration lower than that of the first clotting time-measuring reagent, wherein
   the first and second clotting time-measuring reagents contain an activator, snake venom, or tissue factor.

9. The reagent kit for detecting lupus anticoagulant according to claim 8, wherein
the activator is selected from the group consisting of ellagic acid, kaolin, celite, and silica.

10. The reagent kit for detecting lupus anticoagulant according to claim 9, wherein
the phospholipid is at least one selected from the group consisting of phosphatidylethanolamine, phosphatidylcholine, and phosphatidylserine.

* * * * *